United States Patent [19]
Sauer

[11] Patent Number: 6,017,336
[45] Date of Patent: Jan. 25, 2000

[54] ABSORBENT ARTICLE HAVING THREE DIMENSIONAL LONGITUDINAL CONTAINMENT BARRIERS

[75] Inventor: Barbara Oakley Sauer, Fremont, Wis.

[73] Assignee: Kimberly-Clark Worldwide, Inc., Neenah, Wis.

[21] Appl. No.: 08/763,960

[22] Filed: Dec. 10, 1996

[51] Int. Cl.⁷ .................................................. A61F 13/15
[52] U.S. Cl. ...................... 604/385.1; 604/378; 604/369; 604/385.2
[58] Field of Search ................... 604/385.1–387, 604/396, 395, 378, 369

[56] References Cited

U.S. PATENT DOCUMENTS

| H1630 | 1/1997 | Roe et al. | 604/385.2 |
|---|---|---|---|
| 810,122 | 1/1906 | Green . | |
| 810,123 | 1/1906 | Green . | |
| 810,125 | 1/1906 | Green . | |
| 810,130 | 1/1906 | Green . | |
| 4,257,418 | 3/1981 | Hessner . | |
| 4,662,877 | 5/1987 | Williams . | |
| 4,681,577 | 7/1987 | Stern et al. | 604/378 |
| 4,762,521 | 8/1988 | Roessler et al. . | |
| 4,778,459 | 10/1988 | Fuisz | 604/378 |
| 4,790,839 | 12/1988 | Ahr | 604/385.1 |
| 4,798,603 | 1/1989 | Meyer et al. | 604/378 |
| 4,892,536 | 1/1990 | DesMarais et al. | 604/385.2 |

(List continued on next page.)

FOREIGN PATENT DOCUMENTS

| 0 486 006 A3 | 5/1992 | European Pat. Off. . | |
|---|---|---|---|
| 0 716 842 A1 | 6/1995 | European Pat. Off. . | |
| 0 692 231 A1 | 1/1996 | European Pat. Off. . | |
| 2561078 | 9/1985 | France | 604/385.1 |
| 3188851 | 8/1991 | Japan | 604/385.1 |
| 94/9179 | 11/1994 | South Africa . | |
| 94/9262 | 11/1994 | South Africa . | |
| 2 284 537 | 6/1995 | United Kingdom . | |
| 2 284 538 | 6/1995 | United Kingdom . | |
| 2 284 550 | 6/1995 | United Kingdom . | |
| 2 284 831 | 6/1995 | United Kingdom | A61F 13/15 |
| 2 287 393 | 9/1995 | United Kingdom . | |
| 2 296 192 | 6/1996 | United Kingdom | A61F 13/15 |
| 2 297 683 | 8/1996 | United Kingdom | A61F 13/15 |
| 9500089 | 1/1995 | WIPO | 604/385.1 |
| WO 96/01095 A1 | 1/1996 | WIPO . | |
| WO 96/01609 | 1/1996 | WIPO . | |

Primary Examiner—Mark O. Polutta
Attorney, Agent, or Firm—Jeffrey B. Curtin

[57] ABSTRACT

An absorbent article includes a pair compression resistant containment barriers which are configured to inhibit the lateral flow of fecal exudates along the surface of the absorbent article. The containment barriers are laterally spaced apart to provide a void space between the wearer's buttocks and the surface of the absorbent article for containing body exudates. Each containment barrier defines a width to height ratio of at least about 0.5 and a compression resistance of at least about 50 percent. The absorbent article may also include a containment dam which is located on the bodyfacing surface of the absorbent article and which is configured to inhibit a longitudinal flow of fecal exudates along the surface of the absorbent article. In a particular embodiment, the containment barriers are located between the topsheet layer and absorbent body of the absorbent article. In such a configuration, the topsheet layer defines an opening which is located at least partially over the containment barriers to receive fecal exudates.

41 Claims, 5 Drawing Sheets

U.S. PATENT DOCUMENTS

| | | | |
|---|---|---|---|
| 4,895,568 | 1/1990 | Enloe | 604/385.1 |
| 4,950,262 | 8/1990 | Takagi | 604/385.1 |
| 4,990,147 | 2/1991 | Freeland | 604/385.2 |
| 5,062,840 | 11/1991 | Holt et al. | 604/385.1 |
| 5,171,236 | 12/1992 | Dreier et al. | 604/369 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | |
| 5,207,663 | 5/1993 | McQueen | 604/385.1 |
| 5,269,775 | 12/1993 | Freeland et al. | 604/385.2 |
| 5,281,208 | 1/1994 | Thompson et al. | 604/378 |
| 5,300,053 | 4/1994 | Genaro | 604/378 |
| 5,304,159 | 4/1994 | Tanji et al. | 604/385.2 |
| 5,304,160 | 4/1994 | Igaue et al. | 604/385.2 |
| 5,306,266 | 4/1994 | Freeland | 604/385.1 |
| 5,330,459 | 7/1994 | Lavon et al. | 604/385.1 |
| 5,330,598 | 7/1994 | Erdman et al. | 156/164 |
| 5,344,516 | 9/1994 | Tanji et al. | 156/164 |
| 5,356,405 | 10/1994 | Thompson et al. | 604/384 |
| 5,366,453 | 11/1994 | Zehner et al. | 604/385.2 |
| 5,391,160 | 2/1995 | Runeman et al. | 604/378 |
| 5,409,476 | 4/1995 | Coates | 604/391 |
| 5,417,680 | 5/1995 | Kimura et al. | 604/385.2 |
| 5,439,458 | 8/1995 | Noel et al. | 604/378 |
| 5,439,459 | 8/1995 | Tanji et al. | 604/385.2 |
| 5,451,442 | 9/1995 | Pieniak et al. | 428/54 |
| 5,476,457 | 12/1995 | Roessler et al. | 604/385.1 |
| 5,509,915 | 4/1996 | Hanson et al. | 604/378 |
| 5,575,785 | 11/1996 | Gryskiewicz | 604/385.2 |
| 5,624,426 | 4/1997 | Roe et al. | 604/385.1 |
| 5,649,918 | 7/1997 | Schleinz | 604/385.1 |
| 5,672,166 | 9/1997 | Vandemoortele | 604/385.2 |

ABSORBENT ARTICLE HAVING THREE DIMENSIONAL LONGITUDINAL CONTAINMENT BARRIERS

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to collect and contain fecal material and avoid leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have also typically included elasticized waistbands and leg cuffs to help reduce the leakage of body exudates.

However, many of such conventional absorbent articles have not been completely satisfactory. For example, many conventional absorbent articles have not completely contained the body exudates within the article during use thereby undesirably resulting in leakage which has soiled the clothes of the wearer. This leakage problem has been particularly evident in the leg regions of such absorbent articles when runny or watery fecal material has been excreted by the wearer during use. Typically, the runny or watery fecal material has been forced laterally and longitudinally outwards from the crotch of the article towards the leg and waist openings in the article due to the forces exerted by the wearer. Such problems are magnified when the wearer is particularly active and continually exerts pressure on the crotch area of the article. The leakage problem has also occurred because such fecal material, which has an affinity for the skin, has traveled along the skin of the wearer and has not been sufficiently contained and controlled within the absorbent article.

Some conventional absorbent articles have included elasticized components and containment or barrier flaps at the leg and waist regions of the article to reduce such leaks. However, such elasticized components and containment flaps have not always completely eliminated leakage from the leg regions of such articles. For example, exudates such as runny fecal material have remained on and been transferred along the skin of the wearer until they escape through small openings between the containment flaps and the body of the wearer. Such openings between the body of the wearer and the containment flaps have been caused by improper fit of the article about the wearer and the movements of the wearer during use. Moreover, such containment flaps have typically not been very resistant to compressive forces and have readily collapsed under the weight of or forces exerted by the wearer. Such collapsing has undesirably allowed the wearer's body to contact the bodyside liner of the article during use which has forced any fecal exudates out of the crotch portion.

As a result, although such leg elastics and containment flaps have improved the performance of such articles, there remains a need to further reduce the number of leaks of fecal material from the leg and waist regions of such absorbent articles.

SUMMARY OF THE INVENTION

In response to the difficulties and problems discussed above, a new disposable absorbent article which includes a pair of longitudinally extending, three dimensional containment barriers for containing and stopping the lateral flow of body exudates and, in particular, runny fecal material has been discovered.

As used herein, the term "compression resistance" refers to the compression resistance value determined according to the Compression Resistance Test set forth below.

In one aspect, the present invention relates to a disposable absorbent article which comprises a pair of longitudinally extending, compression resistant containment barriers. The containment barriers are located in a laterally spaced apart relation on the bodyfacing surface of the absorbent article and are configured to provide a void space between the wearer's buttocks and the bodyfacing surface of the absorbent article for containing fecal exudates. Each of the containment barriers defines a length, a width, a height, a width to height ratio of at least about 0.5, and a compression resistance of at least about 50 percent. In a particular embodiment, the containment barriers are laterally spaced apart a distance of no more than about 8 centimeters. In another embodiment, the inner edge of each of the containment barriers defines a plurality of recesses which provide additional void space between the containment barriers and increased flexibility of the containment barriers.

The absorbent article may further comprise at least one compression resistant, containment dam which is located on the bodyfacing surface of the absorbent article. The containment dam is configured to inhibit the longitudinal flow of fecal exudates along the bodyfacing surface of the absorbent article. The containment dam may be located longitudinally inward from the end edge of the rear waist section of the absorbent article a distance of at least about 10 percent of the length of the absorbent article.

In another aspect, the present invention relates to a disposable absorbent article having a front waist section, a rear waist section, an intermediate section which interconnects the front and rear waist sections, a pair of longitudinally opposed end edges, and a pair of laterally opposed side edges. The article comprises a backsheet layer, a liquid permeable topsheet layer which is connected in superposed relation to the backsheet layer, an absorbent body which is located between the topsheet layer and the backsheet layer, and a pair of longitudinally extending, compression resistant containment barriers which are located in a laterally spaced apart relation on the topsheet layer. The containment barriers are configured to provide a void space between the wearer's buttocks and the topsheet layer of the absorbent article for containing fecal exudates. The article further comprises a pair of longitudinally extending containment flaps which are located along the side edges of the absorbent article laterally outwards from the containment barriers. The containment flaps define an attached edge which is at least partially attached to the side edges of the absorbent article, a free edge which remains unattached to the side edges in at least the intermediate section of the absorbent article, and at least one elastic member which is configured to maintain the free edge in a generally perpendicular, spaced away relationship from the side edge of the absorbent article in the intermediate section. In a particular embodiment, the containment barriers define a length, a width, a height, a width to height ratio of at least about 0.5, and a compression resistance of at least about 50 percent.

In yet another aspect, the present invention relates to a disposable absorbent article having a front waist section, a rear waist section, an intermediate section which interconnects the front and rear waist sections, a pair of longitudinally opposed end edges, and a pair of laterally opposed side edges. The article comprises a backsheet layer, a topsheet layer which is connected in superposed relation to the backsheet layer and which defines an opening therein for receiving fecal exudates, an absorbent body which is located between the topsheet layer and the backsheet layer, and a pair of longitudinally extending, compression resistant containment barriers. The containment barriers are located in a laterally spaced apart relation between the absorbent body and the topsheet layer of the absorbent article and are configured to provide a void space between the wearer's buttocks and the absorbent body of the absorbent article for containing fecal exudates. In a particular embodiment, the containment barriers define a length, a width, a height, a width to height ratio of at least about 0.5, and a compression resistance of at least about 50 percent.

The various aspects of the present invention can advantageously provide an absorbent article which effectively absorbs and contains body exudates. In particular, the present invention includes a pair of longitudinally extending, compression resistant containment barriers which reduce the lateral flow of body exudates and space the wearer's body from the absorbent body of the absorbent article to provide a void space for containing such exudates. As a result, the absorbent articles of the various aspects of the present invention have reduced leakage when compared to conventional absorbent articles which results in improved consumer preference.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
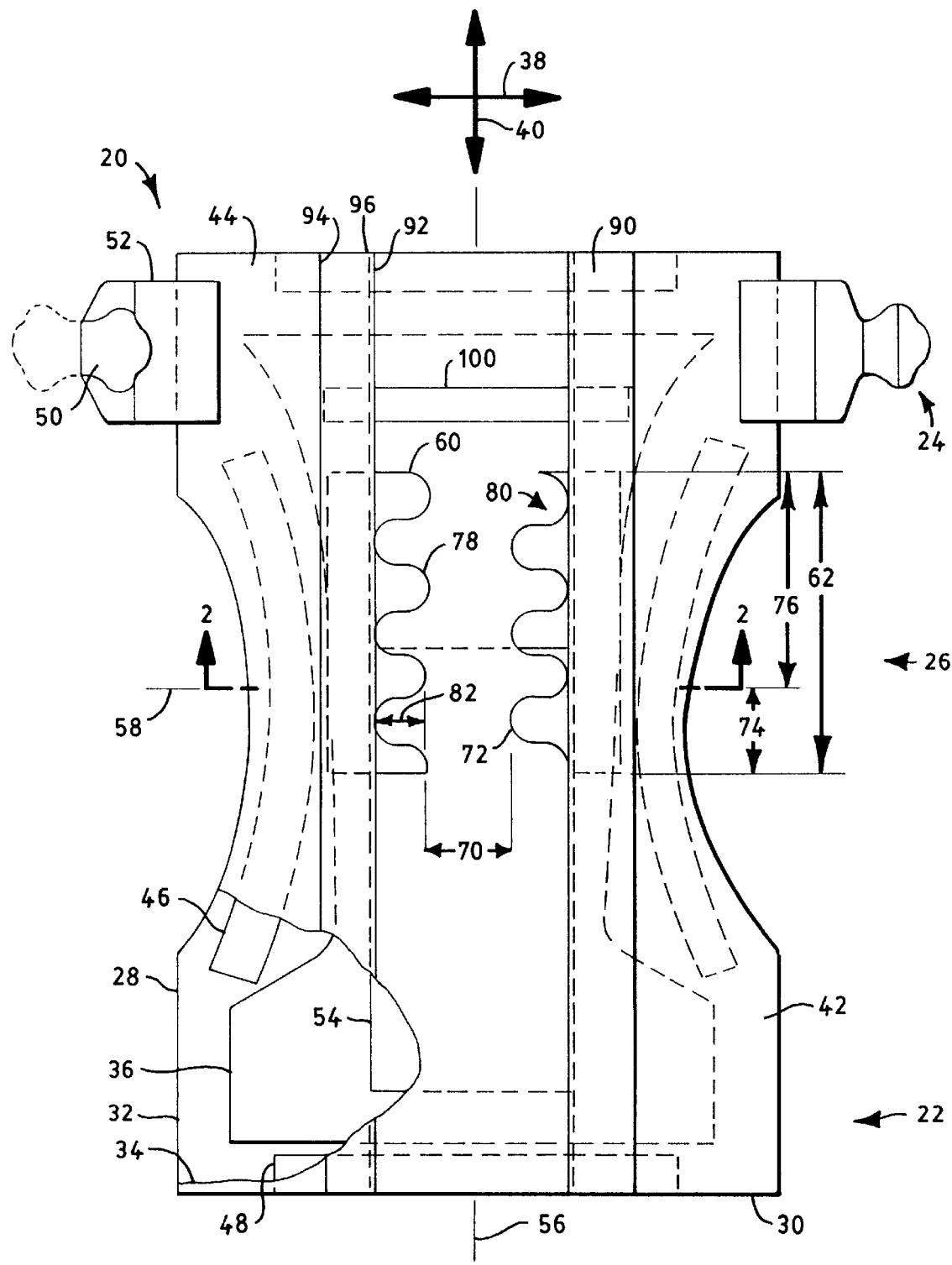
FIG. 1 representatively shows a partially cut away, top plan view of an absorbent article according to one embodiment of the invention.
Figure 2:
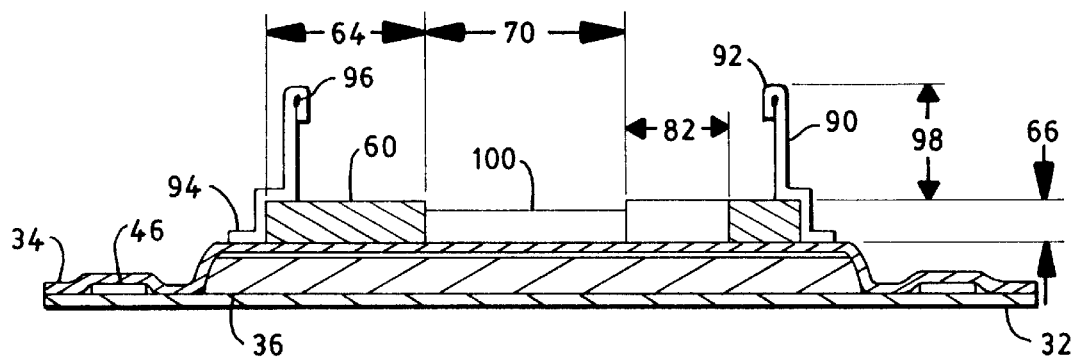
FIG. 2 representatively shows a sectional view of the absorbent article of FIG. 1 taken along line 2—2.

With reference to FIGS. 1 and 2, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The diaper 20 also defines a lateral direction 38 and a longitudinal direction 40 and a longitudinal centerline 56 and a lateral centerline 58. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIG. 1, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIG. 1, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20.

The diaper 20 may also include a pair of elasticized, longitudinally extending containment flaps 90 which are configured to maintain an upright, perpendicular arrangement in at least the intermediate section 26 of the diaper 20 to serve as an additional barrier to the lateral flow of body exudates. The containment flaps include a free edge 92 which remains unattached to the topsheet 34 of the diaper 20 in at least the intermediate section 26 of the diaper and an attached edge 94 which may remain attached to the topsheet 34 over substantially the entire length of the containment flap 90. The containment flaps 90 also include an elastic means 96 which is configured to maintain the free edge 92 spaced away from the topsheet 34 in at least the intermediate section 26 of the diaper 20 to maintain the upright arrangement to provide a barrier against the lateral flow of exudates.

The diaper 20 may further include a surge management layer 54 positioned between the topsheet 34 and the absorbent body 36 which is configured to efficiently hold and distribute liquid exudates to the absorbent body 36. The surge management layer 54 can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20, as representatively illustrated in FIGS. 1 and 2, further includes a pair of longitudinally extending, compression resistant containment barriers 60 located along the side edges 28 of the diaper 20 at least in the intermediate section of the diaper 20. The containment barriers 60 are configured to reduce the lateral flow of fecal exudates out of the leg regions of the diaper 20 and provide a void space between the buttocks of the wearer and the absorbent portion of the diaper 20 during use. The void space is configured to contain body exudates and, in particular, fecal exudates until they can be absorbed or desorbed by the absorbent body 36 of the diaper 20. The diaper 20 as representatively illustrated in FIGS. 1 and 2, may further include at least one containment dam 100 which is configured to inhibit the longitudinal flow of fecal exudates into regions of the diaper 20 such as the rear waist section 24 to more effectively contain such material within the diaper 20.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; and U.S. Pat. No. 5,509,915 issued Apr. 23, 1996, to Hanson et al., the disclosures of which are herein incorporated by reference to the extent they are consistent herewith. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 article by employing the above-identified attachment mechanisms.

The backsheet 32 of the diaper 20, as representatively illustrated in FIG. 1, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIG. 1, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearer's skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation Triton X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The diaper 20 of the present invention also includes at least one longitudinally extending containment barrier 60. For example, as representatively illustrated in FIGS. 1 and 2, the diaper 20 may include a pair of longitudinally extending containment barriers 60 which are positioned in a laterally spaced apart relation on the diaper 20. Each containment barrier 60 may be a single longitudinally extending barrier or may include two or more longitudinally extending barriers which are located along the side edges 28 of the diaper 20. For example, each containment barrier 60 of the diaper 20 may include from 1 to about 10 individual barriers located along each side edge 28 of the diaper. In such a configuration, the individual barriers may be arranged in any configuration along the side edges 28 of the diaper 20 to conform to the wearer's body. Suitable configurations include linear, curvilinear, staggered, diverging, converging and the like, and combinations thereof.

The containment barriers 60, are configured to provide a seal with the wearer's buttock to help reduce leaks along the side edges 28 of the diaper 20 by preventing the lateral flow of fecal exudates. In addition, the containment barriers 60 are at least partially resistant to compression to provide a void space between the containment barriers 60, the wearer's buttocks and the topsheet 34 of the diaper 20 in use. The void space is configured to receive and contain fecal exudates. At least a portion of the fecal exudates may then be absorbed or desorbed by the absorbent body 36. Desirably, the containment barriers 60 are configured to contain substantially all of the solid fecal exudates in the target zone of the diaper 20. As used herein, the term "target zone" refers to that portion of the diaper 20 which is configured to directly receive the insult of fecal exudates from the wearer and generally is located in the crotch portion of the diaper 20. In particular, the target zone may extend from about 5 to about 10 centimeters in length with about one third of it's length extending longitudinally from the lateral centerline 58 of the diaper towards the front waist section 22 of the diaper 20 and the remainder extending longitudinally towards the rear waist section 24 of the diaper 20.

In the embodiments illustrated in FIGS. 1 and 2, two containment barriers 60 are positioned on the bodyfacing surface of the topsheet 34 of the diaper 20 in a laterally spaced apart relationship. The containment barriers 60 may remain substantially unattached to the topsheet 34 or may be attached to the topsheet 34 using conventional means described above such as adhesive. Desirably, the containment barriers 60 are secured to the topsheet 34 in a manner which stabilizes the barriers 60 and maintains the barriers 60 in an upright position during use. Alternatively, as representatively illustrated in FIGS. 6 and 7, the containment barriers 60 may be located between the topsheet 34 and the absorbent body 36 of the diaper 20. In such an arrangement, the containment barriers 60 may be provided directly by the absorbent body 36 of the diaper 20. For example, the absorbent body 36 may include two laterally spaced apart, longitudinally extending portions which define a greater thickness or height to provide the containment barriers 60 of the different aspects of the present invention. In configurations wherein the containment barriers 60 are located between the topsheet 34 and the absorbent body 36 of the diaper 20, the diaper 20 may include an additional layer or sheet of material (not illustrated) between the containment barriers 60 and the absorbent body 36. Such a layer may be provided by materials known to those skilled in the art such as those described above as being suitable for use as the topsheet 34 of the diaper 20.

Typically, the containment barriers 60 are located along the side edges 28 of the diaper 20 in the intermediate section 26 of the diaper 20 and generally extend in the longitudinal direction 40. Desirably, the containment barriers 60 are located on the side edges 28 of the diaper in at least the target zone of the diaper as described above. In particular, the containment barriers 60 or group of containment barriers 60 along each side edge 28 of the diaper 20 may be located on the diaper 20 such that about one third of their length extends longitudinally from the lateral centerline 58 of the diaper 20 towards the front waist section 22 of the diaper 20 and the remainder extends longitudinally towards the rear waist section 24 of the diaper 20.

Desirably, the containment barriers 60 are configured to maintain contact with the wearer during use to provide improved resistance to the explosive lateral flow of fecal exudates which may occur due to the compressive forces exerted by the wearer while sitting. To reduce the effect of the compressive forces exerted by the wearer, the containment barriers 60 are laterally spaced apart such that, when the diaper is being worn by a wearer, a void space is created between the wearer's buttocks and the containment barriers 60 and absorbent body 36 of the diaper. The size of the void space is dependent upon the height and length of the containment barriers 60, the lateral distance between the inner edges of the containment barriers 60, the size of any voids in the containment barriers 60, and the compression resistance of the containment barriers 60 in use. Thus, the lateral distance between the barriers is an important factor to ensure that the void space between the containment barriers 60 is sufficient for containing the fecal exudates while not being too great that the wearer's buttocks push between the containment barriers 60 and undesirably reduce the void space thereby exerting compressive forces on the fecal exudates.

For example as representatively illustrated in FIG. 1, the inner edges 72 of the containment barriers 60 may be laterally spaced apart a distance 70 of from about 2 to about 10 centimeters, desirably no more than about 8 centimeters and more desirably no more than about 6 centimeters for improved performance. If the containment barriers 60 are positioned in a nonlinear or diverging configuration, it is particularly important to maintain the distance 70 between the containment barriers 60 in at least the portion of the diaper 20 intended to contact the buttocks of the wearer in use. This portion generally may extend from about 5 to about 15 centimeters in length longitudinally from the lateral centerline 58 of the diaper towards the rear waist section 24 of the diaper 20.

As a result, the containment barriers 60 are typically located at least partially on top of the absorbent body 36 of the diaper 20 near the longitudinal sides of the absorbent body 36. Alternatively, if the width of the absorbent body 36 is fairly narrow in the intermediate section 26 of the diaper 20, the containment barriers may extend laterally beyond the longitudinal sides of the absorbent body. Typically, it is desirable that at least the inner edges of the containment barriers 60 are located on the absorbent body 36 such that any fecal exudates contained in the void space between the wearer's body and the containment barriers 60 and the absorbent body 36 of the diaper 20 are absorbed or desorbed by the absorbent body 36. Such a configuration is desirable to allow the containment barriers 60 to provide a gentle seal with the wearer's body to inhibit the lateral flow of fecal material out the side edges 28 of the diaper 20 while maintaining sufficient void space between the wearer's body and the containment barriers 60 and the absorbent body 36. Desirably, the containment barriers 60 are located such that they maintain a pressure contact with the wearer's body when the wearer is sitting to create a good seal against the lateral flow of fecal exudates. It is also desirable that the body facing surface of the containment barriers 60 have an affinity for the skin of the wearer to help maintain contact with the wearer's body in use and yet be nonocclusive to the skin.

The containment barriers 60 may have any shape which provides the desired void space between the wearer's buttocks and the absorbent body 36 of the diaper 20 and the desired inhibition of the lateral flow of fecal exudates. Suitable cross sections for the longitudinally extending containment barriers 60 include circular, semi-circular, oval, elliptical, triangular, rectangular, square, and the like. Desirably, the body facing edges of the containment barriers 60 are curved to reduce irritation and provide improved comfort to the wearer. The surfaces of the containment barriers 60 may also have any desired contour or configuration such as angled, sinusoidal, or egg carton shaped. In the illustrated embodiments, each containment barrier 60 generally defines a length 62, a width 64, a height 66, and an inner and outer edge 72. As used herein, the term "length" for each containment barrier 60 refers to the overall length of the barrier or series of barriers in the longitudinal direction. As discussed above, the length 62 and height 66 of the containment barriers 60 along with the lateral spacing between the barriers are important because they define the void space created to contain the fecal exudates. Desirably, the area of the void space is maximized while the height 66 of the containment barriers 60 is minimized to provide sufficient void volume while not causing excessive discomfort to the wearer.

The length 62 of the containment barriers 60 must be sufficient to block at least the majority of the passageways out the side edges 28 of the diaper through which the fecal exudates may flow. Desirably, the length 62 of the containment barriers is at least sufficient to block the lateral flow of fecal exudates from the target zone of the diaper 20. For example, on a diaper article intended to be worn by a medium sized infant, the containment barriers 60 may define a length 62 of at least about 3 centimeters and desirably at least about 7 centimeters. Desirably, the containment barriers 60 define a length 62 which is at least about 15 percent of the length of the diaper 20 as measured along the longitudinal centerline 56 of the diaper 20. In a particular embodiment, the containment barriers 60 define a length which is equal to about 25 percent of the length of the diaper 20 as measured along the longitudinal centerline 56 of the diaper 20 for improved performance.

Figure 6:
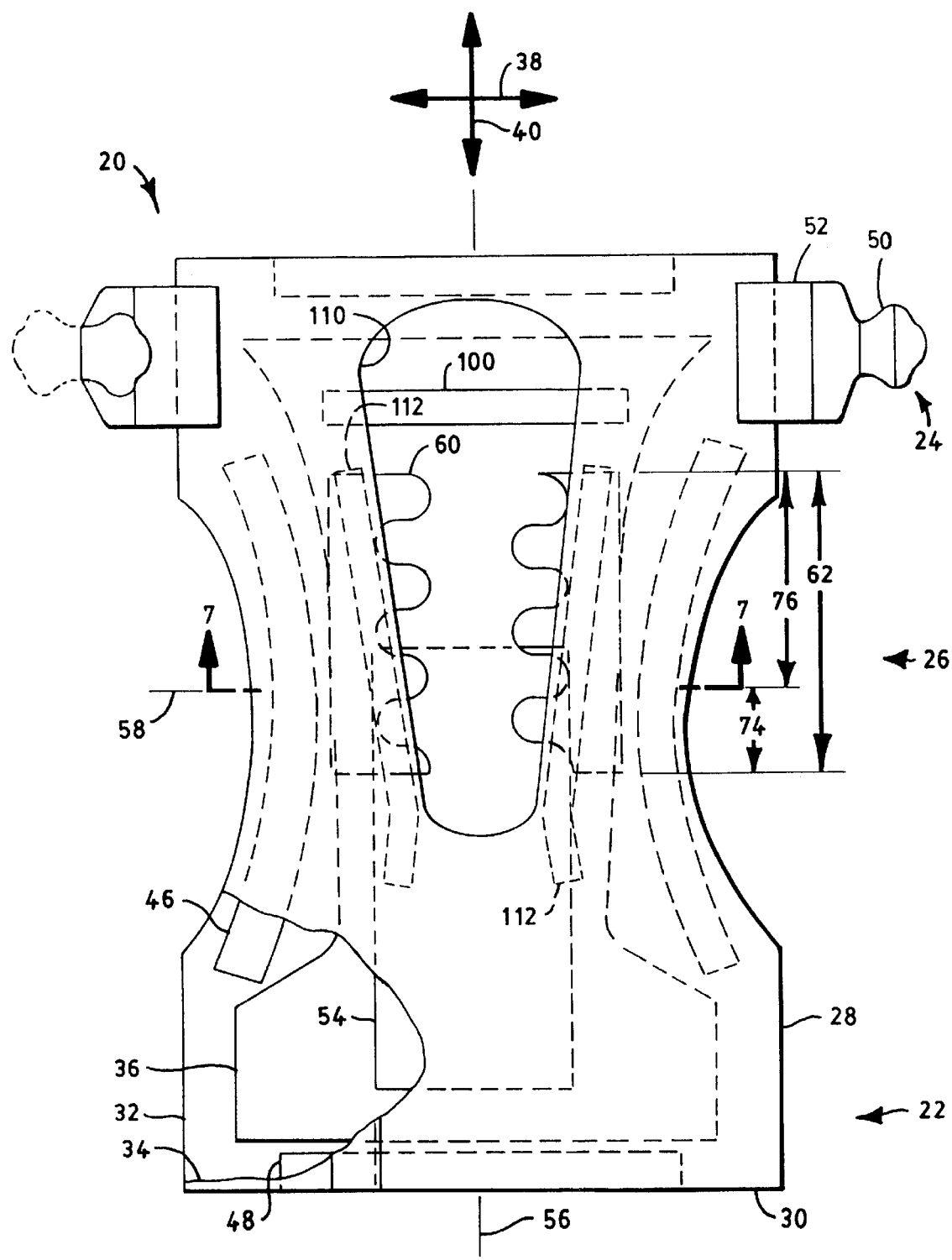
FIG. 6 representatively shows a partially cut away, top plan view of an absorbent article according to another embodiment of the invention.

As representatively illustrated in FIGS. 1 and 6, the containment barriers 60 are desirably located along the side edges 28 of the diaper such that about one third of their length extends longitudinally from the lateral centerline 58 of the diaper 20 towards the front waist section 22 of the diaper 20 and the remainder extends longitudinally towards the rear waist section 24 of the diaper 20. Desirably, at least about 50 percent and more desirably from about 60 to about 80 percent of the length 62 of the containment barriers 60 is located rearward of the lateral centerline 58 of the diaper 20 for improved performance. As used herein, the term "rearward" relates to the direction extending from the lateral centerline 58 towards the rear waist section 24 of the diaper 20. For example, the containment barriers 60 may extend longitudinally from the lateral centerline 58 of the diaper 20 towards the front waist section 22 of the diaper 20 a length 74 of from about 1 to about 5 centimeters and the from the lateral centerline 58 of the diaper 20 towards the rear waist section 24 of the diaper 20 a length 76 of from about 5 to about 14 centimeters.

The height 66 of the containment barriers 60 must be sufficient to provide the desired void space between the wearers buttocks and the absorbent body 36 of the diaper 20 and the desired seal against the body of the wearer to resist the lateral flow of fecal exudates even when the diaper is subjected to the compressive forces of the wearer. However excessive height 66 of the containment barrier 66 may undesirably result in excessive irritation and redmarking of the skin of the wearer.

Desirably, the containment barriers 60 may define an uncompressed height 66 of from about 0.3 to about 2.5 centimeters, more desirably at least about 0.5 centimeters and even more desirably at least about 0.75 centimeters.

Figure 3:
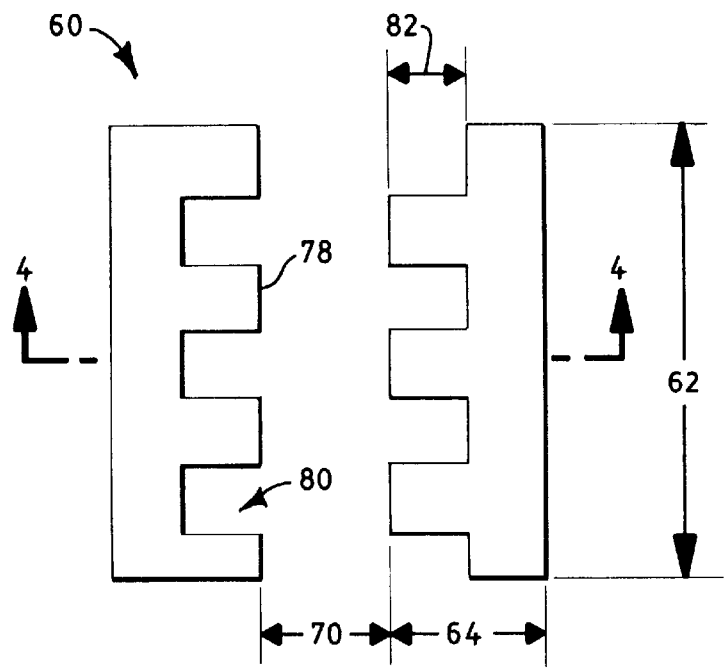
FIG. 3 representatively shows a pair of containment barriers for use on absorbent articles according to another embodiment of the invention.
Figure 4:
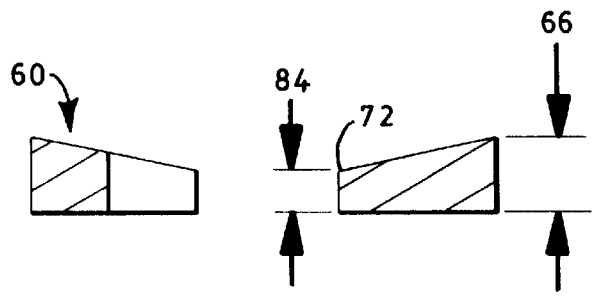
FIG. 4 representatively shows a sectional view of the containment barriers of FIG. 3 taken along line 4—4.
Figure 5:
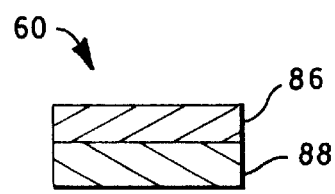
FIG. 5 representatively shows a sectional view of a containment barrier according to another embodiment of the invention.

In a particular embodiment as representatively illustrated in FIGS. 3 and 4, the containment barriers 60 may be constructed such that the height 84 of the inner edge of the barrier 60 is less than the height 66 of the outer edge of the containment barrier 60. As used herein, reference to the "inner edge" of the containment barriers 60 refers to the longitudinally extending side edge of the containment barriers closest to the longitudinal centerline 56 of the diaper 20 while reference to the "outer edge" of the containment barriers 60 refers to the longitudinally extending side edge of the containment barriers located laterally outwards from the inner edge and more distant from the longitudinal centerline 56 of the diaper 20 than the inner edge. Applicants have discovered that slanting the bodyfacing surface of the containment barriers 60 in such a manner provides improved comfort for the wearer by better conforming to the buttocks of the wearer. Desirably, the ratio of the height 66 of the outer edge to the height 84 of the inner edge of the containment barrier 60 is at least about 1.1 and more desirably at least about 1.25 for improved performance. In such a configuration, it remains desirable that the height 84 of the inner edge of the containment barriers 60 be at least about 0.5 centimeters to effectively provide the desired void space between the buttocks of the wearer and the absorbent body 36 of the diaper 20.

The width 64 of the containment barriers 60 provides stability to the barriers 60 such that they do not fold over or bend during use. For example, the containment barriers 60 define a width 64 of from about 0.5 to about 2.5 centimeters, desirably at least about 0.6 centimeters and more desirably at least about 1.0 centimeters for improved performance. Desirably, the containment barriers 60 define a width 64 which is at least about 7 percent of the width of the diaper 20 as measured along the lateral centerline 58 of the diaper 20. In a particular embodiment, the containment barriers 60 define a width 64 which is equal to about 16 percent of the width of the diaper 20 as measured along the lateral centerline 58 of the diaper 20 for improved performance. Widths less than those set forth above may undesirably result in instability of the barrier and irritation of the skin of the wearer during use while widths greater than those set forth above may undesirably result in a diaper having a wide crotch portion which may adversely affect fit and performance.

To maintain the stability of the containment barriers 60 during use, the containment barriers 60 define a width to height ratio of at least about 0.5, desirably at least about 0.75, and more desirably at least about 1.0. Width to height ratios less than those set forth above may undesirably result in the containment barriers 60 bending or folding over which reduces the void space between the wearer's body and the absorbent body 36 and results in increased lateral flow of fecal exudates over the barriers 60.

In one embodiment of the present invention, the containment barriers 60 may be held or anchored in place to improve the stability of the containment barriers by one or more sheets of material such as a nonwoven material or foam material which extends at least partially over the bodyfacing surface of the containment barriers 60 and which may be attached to the topsheet 34 or absorbent body 36 of the diaper 20. The use of such material to anchor the barriers in place can help minimize the required width to height ratio for maintaining the stability of the barriers. Desirably, the sheet of material conforms to the shape and contour of the containment barriers 60 to prevent any gaps from forming between the sheet of material and the containment barriers 60. For example, the sheet of material may be adhesively bonded to the outer surface of the containment barriers 60 to prevent such gaps. It is further desirable that the sheet of material surround and secure at least three of the sides of the containment barriers 60 for improved stability. The sheet or sheets of material may be provided by any material which is relatively soft and strong to anchor the barriers 60 in place and provide a cushion between the barriers 60 and the body of the wearer. Desirably, the sheet of material is a hydrophobic material such that the sheet is not configured to assist in drawing the fecal exudates over the top of the barriers 60.

As representatively illustrated in FIGS. 1–3, the containment barriers 60 of the different aspects of the present invention may also include at least one recess 78 which extends from the inner edge towards the outer edge of the containment barrier 60. For example, as illustrated, the inner edge of each containment barrier 60 may define a plurality of recess 78 which define a width 80 in the longitudinal direction 40 and a depth 82 in the lateral direction 38 away from the longitudinal centerline 56 of the diaper 20. The recesses 78 are configured to provide additional void space between the wearer's buttocks and the containment barriers 60 and absorbent body 36 of the diaper 20. In a particularly desirable configuration, the containment barriers 60 define from about 2 to about 10 recesses along their length for improved performance.

The inner edge of the containment barriers 60 may have any desired shape which provides the recesses 78 to provide the increased void space and flexibility to the diaper 20. Suitable shapes include sinusoidal, stair step, ladder, and V notched as are well known to those skilled in the art. In embodiment wherein each containment barrier 60 includes multiple individual barriers, each barrier may have a "C" shape which provides the desired compression resistance and structural support while maintaining sufficient void space. As illustrated in FIGS. 1 and 2, the inner edge of the containment barriers 60 may define a sinusoidal type pattern which provides a plurality of recesses 78. Alternatively, as representatively illustrated in FIG. 3, the inner edge of the containment barriers 60 may define a ladder type shape to provide each recess 78. The ladder type shape may be provided by a square or rectangular cut into the inner edge of each containment barrier 60. To provide the desired void volume without being too wide or deep so as to allow the wearer's buttocks to fill the recess or void space, the width 80 of the recesses 78 is at least about 0.5 centimeters and generally from about 0.5 to about 2 centimeters and the depth 82 of the recesses is at least about 0.5 centimeters and generally from about 0.5 to about 1.5 centimeters for improved performance.

It is also desirable that the containment barriers 60 be flexible such that they readily conform to the shape and contours of the wearer's buttocks. If the flexibility of the containment barriers 60 is too low, the containment barriers may not effectively conform to the body of the wearer and may cause undesired leakage and redmarking and irritation of the skin of the wearer.

To provide additional void volume, the containment barrier 60 may further include at least one hole or tunnel extending laterally into the barriers from the inside edge of the barriers. For example each containment barrier may include from 1 to about 5 holes or tunnels therein for improved containment of fecal exudates. The holes or tunnels may define a diameter which is from about 25 to about 75 percent of the height 66 of the containment barriers 60 and may or may not extend completely through the width of the containment barrier 60.

The containment barriers 60 are configured to maintain their shape during use to effectively provide the void space between the wearer's buttocks and the absorbent body 36 of the diaper 20 and inhibit the lateral flow of fecal exudates. For example, it is desirable that the containment barriers 60 be capable of resisting any z-directional compressive forces which may be exerted by the wearer during use. In a particular embodiment, the containment barriers 60 define a z-directional compression resistance of at least about 50 percent, desirably at least about 70 percent, and more desirably at least about 85 percent. For example, the containment barriers 60 may define a compression resistance of from about 50 to about 95 percent. When the containment barriers have a compression resistance less than the values set forth above, the containment barriers may collapse during usage which adversely affects the ability of the barriers to provide the desired void space and resist the lateral flow of fecal exudates. Whereas, if the compression resistance of the containment barriers is too high, the containment barriers may cause undesired redmarking and irritation of the skin of the wearer.

Desirably, the containment barriers 60 have sufficient compression resilience such that the height 66 of the barriers 60 remains at least about 0.3 centimeters and desirably at least about 0.5 centimeters when the containment barriers 60 are under a compressive load of about 350 grams per square centimeter.

The containment barriers 60 of the different aspects of the present invention, as representatively illustrated in FIGS. 1–7, may be made from any material which provides the desired shape and level of compression resistance. Suitable materials include foams, fibrous webs of natural or synthetic fibers or combinations thereof, and multiple layer fibrous webs. For example, the containment barriers may be a crosslinked polyethylene foam material which is commercially available from Sentinel Foams, a business having offices located in Hyannis, Mass., under the trade designation EMR NAT. Alternatively, as described above, the containment barriers 60 may be provided by absorbent materials such as those described above as being suitable for the absorbent body of the diaper 20 of the present invention.

The containment barriers 60 may also be provided by a laminate or composite of materials which can be configured to provide different properties to the barriers 60. For example, in a particular embodiment as representatively illustrated in FIG. 5, the containment barriers 60 may include a first layer 86 which is configured to contact or face the buttocks of the wearer and a second layer 88 which is located on the bodyfacing surface of the diaper 20 which may be the topsheet 34 or absorbent body 36 of the diaper 20. In such a configuration, the first layer 86 may be configured to provide a soft, gentle contact with the wearer's buttocks while the second layer 88 may be configured to provide the desired compression resistance to effectively provide the void space between the wearer's buttocks and the absorbent body 36 of the diaper 20 and inhibit the lateral flow of fecal exudates. For example, the first layer 86 may define a height or thickness of from about 0.1 to about 0.5 centimeters and be configured to define a compression resistance of no more than about 60 percent and desirably no more than about 50 percent to provide a soft contact with the wearer. While the second layer 88 may define a height or thickness of from about 0.1 to about 2.0 centimeters and be configured to provide a compression resistance of at least about 70 percent and desirably at least about 85 percent for improved performance.

In such a configuration, the first layer 86 may be constructed of a nonwoven or foam material as described above as being suitable for the topsheet or similar materials known to those skilled in the art while the second layer 88 may be constructed of any suitable material having the desired compression resistance such as those described above as being suitable for the containment barrier 60.

As representatively illustrated in FIGS. 1 and 2, the diaper 20 of the different aspects of the present invention may also include a pair of elasticized, longitudinally-extending containment flaps 90. The containment flaps 90 are configured to maintain an upright, perpendicular arrangement in at least the intermediate section 26 of the diaper 20 to serve as an additional barrier to the lateral flow of body exudates. In the illustrated embodiment, a pair of containment flaps 90 are attached to the topsheet 34 of the diaper 20 along the side edges 28 of the diaper 20. Suitable arrangements and constructions for containment flaps 90 are described, for example, in U.S. Pat. No. 4,704,116 issued Nov. 3, 1987, to K. Enloe, the disclosure of which is hereby incorporated by reference to the extent it is consistent herewith.

The containment flaps 90 are attached to the topsheet 34 along attached edges 94. The containment flaps 90 also include free edges 92 which are configured to remain unattached to the other components of the diaper 20 in at least the intermediate section 26 of the diaper 20. The free edges 92 of the containment flaps 90 include a flap elastic member 96 which can comprise one or more strands of individual elastic material. For example, a suitable elastic strand may be composed of a 470 decitex LYCRA elastomer which is available from E. I. DuPont de Nemours. The elastic member 96 is connected to the free edge 92 in an elastically contractible condition such that the contraction of the elastic member 96 contracts and gathers the free edge 92. As a result, the free edge 92 of the containment flaps tends to position itself in a spaced relation away from the topsheet 34 of the diaper 20 toward a generally upright and approximately perpendicular configuration, especially in the intermediate section 26 of the diaper 20.

As representatively illustrated in FIGS. 1 and 2, the containment flaps 90 are desirably located along the side edges 28 of the diaper 20 laterally outwards from the containment barriers 60 for improved containment of body exudates and, in particular, fecal exudates. In such a configuration, it is desirable that, in an unrestrained configuration, the containment flaps 90 extend in a generally perpendicular manner above the containment barriers 60 a distance 98 of at least about 0.2 centimeters and more desirably at least about 1.0 centimeters for improved containment of body exudates. The existence of the containment barriers 60 in the diaper of the present invention allows the containment flaps 90 to extend a greater distance 98 than conventional containment flaps because the containment barriers 60 prevent at least a portion of the containment flaps 90 from folding inwardly and overlapping with each other. The containment flaps 90 may also be located laterally outward from the barriers 60 to provide additional void space between the flaps 90 and the outer edges of the barriers 60.

In the various aspects of the invention, the containment flaps may be constructed of a fibrous material which is similar to those materials described as being suitable for the topsheet 34. Other conventional films such as polymeric films may also be employed. In the illustrated embodiment, the containment flaps 90 are constructed of a spunbond-meltblown-spunbond laminate material composed of polypropylene fibers and having a basis weight of about 25 grams per square meter.

Figure 7:
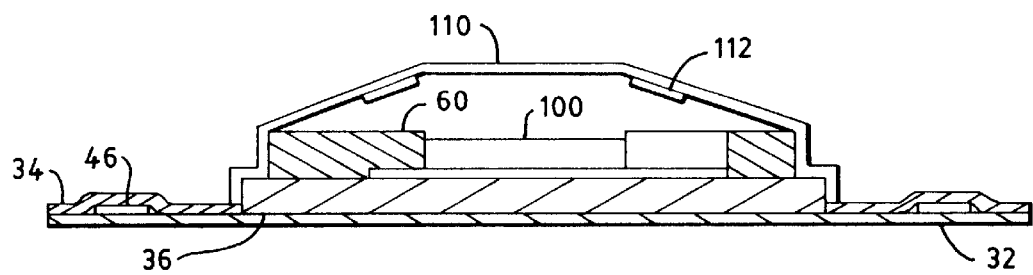
FIG. 7 representatively shows a sectional view of the absorbent article of FIG. 6 taken along line 7—7.

In another embodiment of the invention as representatively illustrated in FIGS. 6 and 7, the containment barriers 60 may be located between the topsheet 34 and the absorbent body 36 of the diaper 20. In such a configuration, the topsheet 34 may extend at least partially over the containment barriers 60 and includes an opening 110 therein which is configured to receive fecal exudates. The opening 110 is located such that the fecal exudates pass through the opening 110 and into the void space created by the containment barriers 60.

The opening 110 in the topsheet 34 generally defines a length in the longitudinal direction 40 and a width in the lateral direction 38. The length and width of the opening 110 must be sufficient to allow fecal exudates to pass through into the void space created between the containment barriers 60. Desirably, the size of the opening 110 is not too large such that the area of the topsheet 34 surrounding the opening 110 prevents excessive contact of the body exudates contained within the diaper 20 with the skin of the wearer. Thus, the dimensions of the opening 110 may be controlled to provide improved skin wellness of the wearer.

Desirably, the opening 110 in the topsheet 34 is similar in size to the target zone of the diaper 20. For example, the opening 110 may define an open area of at least about 10 square centimeters and desirably from about 20 to about 50 square centimeters. On a diaper article intended to be worn by a medium sized infant, the opening may define a length along the longitudinal centerline 56 of the diaper 20 of at least about 4 centimeters and desirably at least about 7 centimeters and a width as measured along the lateral centerline 58 of the diaper 20 of from about 1.0 to about 10 centimeters and desirably from about 2.5 to about 7.5 centimeters. Desirably, the opening 110 defines a length along the longitudinal centerline 56 which is at least about 20 percent of the length of the diaper 20 as measured along the longitudinal centerline 56 of the diaper 20 and a width which is at least about 20 percent of the width of the diaper 20 as measured along the lateral centerline 58 of the diaper 20 for improved performance.

As representatively illustrated in FIGS. 6 and 7, the opening 110 in the topsheet 34 is desirably located such that about one third of it's length extends longitudinally from the lateral centerline 58 of the diaper 20 towards the front waist section 22 of the diaper 20 and the remainder extends longitudinally towards the rear waist section 24 of the diaper 20. Desirably, at least about 50 percent and more desirably from about 60 to about 70 percent of the length of the opening 110 is located rearward of the lateral centerline 58 of the diaper 20 for improved performance.

The opening 110 may have any shape which is capable of receiving the fecal exudates. Suitable shapes include circular, oval, elliptical, square, rectangular and the like. In a particular embodiment as representatively illustrated in FIG. 6, the laterally opposed side edges of the opening 110 diverge from each other laterally outward in the rear waist section 24 of the diaper 20. Such a configuration has been found to better fit the buttocks of the wearer which may provide improved reception and containment of the fecal exudates.

As representatively illustrated in FIGS. 6 and 7, the topsheet 34 in such a configuration may include at least one elastic member 112 which can comprise one or more strands of individual elastic material. For example, a suitable elastic strand may be composed of a 470 decitex LYCRA elastomer which is available from E. I. DuPont de Nemours. The elastic member 112 may be connected to the edge of the opening 110 in the topsheet 34 in an elastically contractible condition such that the contraction of the elastic member 112 contracts and gathers the topsheet 34. Desirably, as illustrated in FIGS. 6 and 7, the topsheet 34 includes an elastic member 112 at least along both of the laterally opposed side edges of the opening 110 in the topsheet 34. In such a configuration, the elastic member 112 can assist in providing a close conforming fit between the topsheet 34 and the buttocks of the wearer which results in improved location of the opening over the anus of the wearer to better receive fecal exudates.

In a particular embodiment, the diaper 20 of the different aspects of the present invention further includes at least one laterally extending containment dam 100, as representatively illustrated in FIGS. 1, 2, 6 and 7. The containment dam 100 is configured to help reduce leaks along the end edges 30 of the diaper 20 by preventing or at least slowing down the longitudinal flow of fecal exudates into regions of the diaper 20 such as the rear waist section 24 to more effectively contain such material within the diaper 20. Desirably, the containment dam 100 is configured to assist the containment barriers 60 of the different aspects of the present invention in containing substantially all of the solid fecal exudates in the target zone of the diaper 20.

In the illustrated embodiments, a single containment dam 100 is positioned on the topsheet 34 or absorbent body 36 of the diaper 20 between the lateral centerline 58 and the end edge 30 in the rear waist section 24 of the diaper 20. In such a configuration, the containment dam 100 is configured to at least reduce if not eliminate the longitudinal flow of fecal exudates to reduce the leakage of fecal exudates from the rear waist section 24 of the diaper 20. The leakage of fecal exudates from the rear waist section 24 of conventional diapers has been a difficult problem to overcome and has been particularly undesirable to the consumer. The diaper 20 of the different aspects of the present invention may further include at least one or more additional containment dams to further reduce such longitudinal flow of fecal exudates.

The containment dam 100 may remain substantially unattached to the topsheet 34 or may be attached to the topsheet 34 using conventional means described above such as adhesive. Desirably, the containment dam 100 is secured to the topsheet 34 in a manner which stabilizes the dam 100 and maintains the dam 100 in an upright position during use. Alternatively as representatively illustrated in FIGS. 6 and 7, the containment dam 100 may be located between the topsheet 34 and the absorbent body 36 of the diaper 20. In such an arrangement, the containment dam 100 may be provided directly by the absorbent body 36 of the diaper 20. For example, the absorbent body 36 may include at least one laterally extending portion which defines a greater thickness or height to provide the containment dam 100. The containment dam 100 may also be held or anchored in place by one or more sheets of material such as described above for anchoring the containment barriers 60.

Typically, the containment dam 100 is located in the rear waist section 24 or intermediate section 26 of the diaper 20 and extends in the lateral direction 38. Desirably, the containment dam 100 is located such that, when the diaper is being worn by a wearer sitting on a flat surface, the containment dam 100 is positioned in close proximity to the line of departure between rear of the wearer's buttocks and the flat surface. In such a position, the containment dam 100 provides improved resistance to the explosive longitudinal flow of fecal exudates which may occur along the gluteal fold of the wearer due to the compressive forces exerted by the wearer while sitting. Desirably, the containment dam 100 is located a distance of at least about 5.0 centimeters, desirably at least about 7.5 centimeters and more desirably at least about 10 centimeters from the end edge 30 in the rear waist section 24 of the diaper 20 towards the front waist section 22 of the diaper 20. Such distances generally correspond to a distance of at least about 10 percent and desirably at least about 15 percent of the total length of the article. For example, the distance the containment dam 100 is located inwardly from the end edge 30 may be from about 10 percent to about 45 percent of the total length of the article.

Such a configuration is desirable to allow the containment dam 100 to inhibit the longitudinal flow of fecal material into the rear waist section 24 of the diaper 20 while allowing sufficient space in the rear waist section 24 to contain any fecal material which passes over the dam 100 and between the dam 100 and the wearer's body. If the distance the containment dam 100 is located from the end edge 30 is too small, the fecal exudates may be able to gain sufficient momentum when pressure is exerted to carry over the top of the dam 100. In addition, if such distance is too small, the dam 100 may not remain in close contact with the buttocks of the wearer when the wearer is sitting which may result in a less than optimum seal with the wearer's body. Desirably, the containment dam 100 is located such that it maintains a pressure contact with the wearer's body when the wearer is sitting to create a good seal against the longitudinal flow of fecal exudates.

The containment dam 100 may have any shape such as those described above with respect to the containment barriers 60 which provides the desired inhibition of the longitudinal flow of fecal material. For example, as representatively illustrated in FIG. 1, the containment dam 100 may define a tubular shape having a circular cross section.

The length of the containment dam 100 must be sufficient to block at least the majority of the passageways through which the fecal exudates may flow. Desirably, the containment dam 100 defines a length which is at least about 10 percent of the width of the diaper 20 as measured along the lateral centerline 58 of the diaper 20. In a particular embodiment wherein the diaper 20 includes a pair of longitudinally extending containment flaps 90, the containment dam 100 defines a length which is substantially equal to or less than the width of the diaper 20 between such containment flaps for improved performance.

The height of the containment dam 100 must be sufficient to provide the desired resistance to the longitudinal flow of fecal exudates even when the diaper is subjected to the compressive forces of the wearer. For example, the containment dam 100 may define a height of at least about 0.5 centimeters and desirably at least about 0.75 centimeters.

To maintain the stability of the containment dam 100 during use, the containment dam 100 desirably defines a width to height ratio of at least about 0.5, desirably at least about 0.75, and more desirably at least about 1.0. Width to height ratios less than those set forth above may undesirably result in the containment dam 100 bending or folding over which may result in increased longitudinal flow of fecal exudates over the dam 100.

Similar to the containment barriers 60, the containment dam 100 is configured to maintain it's shape during use to effectively inhibit the flow of fecal exudates. For example, it is desirable that the containment dam 100 be capable of resisting any z-directional compressive forces which may be exerted by the wearer during use. In a particular embodiment, the containment dam 100 defines a z-directional compression resistance of at least about 50 percent, desirably at least about 70 percent, and more desirably at least about 85 percent. Desirably, the containment dam 100 has sufficient compression resilience such that the height of the dam 100 remains at least about 0.3 centimeters and desirably at least about 0.5 centimeters when the containment dam 100 is under a compressive load of about 350 grams per square centimeter. The containment dam 100 may be made from any material which provides the desired shape and level of compression resistance such as those described above as being suitable for the containment barriers 60. For example, the containment dam may be a crosslinked polyethylene foam material which is commercially available from Sentinel Foams under the trade designation EMR NAT.

Accordingly, the different aspects of the present invention advantageously provide an absorbent article having improved containment and control of body exudates and, in particular, fecal material. The containment barriers of the present invention are resistant to compression and flexible to effectively provide a void space between the buttocks of the wearer and the absorbent body of the article and inhibit the lateral flow of fecal exudates. As a result, absorbent articles made according to the present invention may have a reduced incidence of leaks in the leg regions of the article.

The different aspects of the present invention may also include a pair of longitudinally extending containment flaps and a waist containment dam in combination with the side containment barriers to further reduce the incidence of leaks. Moreover, the topsheet or bodyside liner of the article of the present invention may be configured to conform to the buttocks of the wearer to better isolate the body exudates from the wearer. In such a configuration, the topsheet of the article includes an opening which is configured to allow fecal exudates to pass through the topsheet and into the void space between the wearer's buttocks and the containment barriers and absorbent body of the article.

Compression Resistance Test

This test is configured to measure the compression resistance of materials intended for use as the containment dam according to the present invention. The compression resistance of the materials indicates the ability of the material to maintain it's shape during use.

A sample of the material intended for use as the containment dam is obtained. The compression resistance of the material is tested in a standard compressometer such as that commercially available from Frazier Precision Instrument Company, a business having offices located in Gaithersburg, Md. Initially, the compressometer is calibrated. The sample of material is then placed in the compressometer which includes a foot which defines a diameter of 3.0 inches. The foot is positioned in contact with the sample of material and the original height of the material is measured and recorded. The foot is then lowered until the pressure on the material is 1.0 pounds per square inch. The compressed height of the material is immediately measured and recorded. The compression resistance value of the material sample is then obtained by dividing the compressed height by the original height and multiplying the result by 100 percent.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. A disposable absorbent article comprising a backsheet, a topsheet connected in superposed relation to said backsheet, an absorbent body located between said topsheet and said backsheet, and a pair of longitudinally extending, compression resistant containment barriers which are located in a laterally spaced apart relation on a bodyfacing surface of said absorbent article and which are configured to provide a void space between a wearer's buttocks and said bodyfacing surface of said absorbent article for containing fecal exudates wherein each of said containment barriers defines a length, a width, a height, a width to height ratio of at least about 0.5, and a compression resistance of at least about 50 percent and an inner edge of each of said containment barriers defines a plurality of recesses which define a depth in a lateral direction towards an outer edge of said respective containment barrier and away from a longitudinal centerline of said absorbent article.

2. The absorbent article according to claim 1 wherein said width to height ratio of each of said containment barriers is at least about 0.75.

3. The absorbent article according to claim 1 wherein said compression resistance of each of said containment barriers is at least about 70 percent.

4. The absorbent article according to claim 1 wherein said width of each of said containment barriers is at least about 7 percent of a width of said absorbent article measured along a lateral centerline of said absorbent article.

5. The absorbent article according to claim 1 wherein said height of each of said containment barriers is at least about 0.5 centimeters.

6. The absorbent article according to claim 1 wherein said length of each of said containment barriers is at least about 15 percent of a length of said absorbent article and wherein at least about 50 percent of said length of each of said containment barriers is located rearward of a lateral centerline of said absorbent article.

7. The absorbent article according to claim 1 wherein said containment barriers are laterally spaced apart a distance of no more than about 8 centimeters.

8. The absorbent article according to claim 1 wherein each of said containment barriers defines an inner edge and an outer edge and wherein said height of said containment barrier at said inner edge is less than said height of said containment barrier at said outer edge.

9. The absorbent article according to claim 1 wherein said containment barriers include a foam material.

10. The absorbent article according to claim 1 wherein each of said containment barriers defines a first layer which is configured to contact said wearer's buttocks and a second layer which is located on said bodyfacing surface of said absorbent article.

11. The absorbent article according to claim 10 wherein said first layer defines a compression resistance of no more than about 60 percent and said second layer defines a compression resistance of at least about 70 percent.

12. The absorbent article according to claim 1 wherein each of said containment barriers includes from about 2 to about 10 recesses.

13. The absorbent article according to claim 1 wherein said depth of each of said recesses is at least about 0.5 centimeters.

14. The absorbent article according to claim 1 wherein each of said recesses defines a width of at least about 0.5 centimeters.

15. The absorbent article according to claim 1 and further comprising at least one compression resistant, containment dam which is located on said bodyfacing surface of said absorbent article and which is configured to inhibit a longitudinal flow of fecal exudates along said bodyfacing surface of said absorbent article.

16. The absorbent article according to claim 15 wherein said containment dam is located longitudinally inward from an end edge of a rear waist section of said absorbent article a distance of at least about 10 percent of a length of said absorbent article.

17. The absorbent article according to claim 15 wherein said containment dam defines a compression resistance of at least about 50 percent.

18. The absorbent article according to claim 15 wherein said containment dam defines a height of at least about 0.5 centimeters.

19. A disposable absorbent article having a front waist section, a rear waist section, an intermediate section which interconnects said front and rear waist sections, a pair of longitudinally opposed end edges, and a pair of laterally opposed side edges, said article comprising:
   a) a backsheet layer;
   b) a liquid permeable topsheet layer which is connected in superposed relation to said backsheet layer;
   c) an absorbent body which is located between said topsheet layer and said backsheet layer;
   d) a pair of longitudinally extending, compression resistant containment barriers which are located in a laterally spaced apart relation on a bodyfacing surface of said topsheet layer of said absorbent article and which are configured to provide a void space between a wearer's buttocks and said topsheet layer of said absorbent article for containing fecal exudates wherein each of said containment barriers defines a compression resistance of at least about 50 percent;
   e) a pair of longitudinally extending containment flaps which are located along said side edges of said absorbent article laterally outwards from said containment barriers and which define an attached edge which is at least partially attached to said side edges of said absorbent article, a free edge which remains unattached to said side edges in at least said intermediate section of said absorbent article, and at least one elastic member which is configured to maintain said free edge in a generally perpendicular, spaced away relationship from said side edge of said absorbent article in said intermediate section; and
   f) at least one laterally extending, compression resistant, containment dam which is located on said bodyfacing surface of said topsheet layer of said absorbent article longitudinally rearward of said containment barriers and longitudinally inward from said end edge in said rear waist section of said absorbent article a distance of at least about 10 percent of a length of said absorbent article and which is configured to inhibit a longitudinal flow of fecal exudates along said topsheet layer of said absorbent article.

20. The absorbent article according to claim 19 wherein said free edge of each of said containment flaps is configured to extend in a generally perpendicular manner above said containment barriers a distance of at least about 0.2 centimeters.

21. An absorbent article according to claim 19 wherein each of said containment barriers defines a length, a width, a height, and a width to height ratio of at least about 0.5.

22. The absorbent article according to claim 21 wherein said width of each of said containment barriers is at least about 7 percent of a width of said absorbent article measured along a lateral centerline of said absorbent article.

23. The absorbent article according to claim 21 wherein said height of each of said containment barriers is at least about 0.5 centimeters.

24. The absorbent article according to claim 21 wherein said length of each of said containment barriers is at least about 15 percent of a length of said absorbent article and wherein at least about 50 percent of said length of each of said containment barriers is located rearward of a lateral centerline of said absorbent article.

25. The absorbent article according to claim 19 wherein said containment barriers are laterally spaced apart a distance of no more than about 8 centimeters.

26. The absorbent article according to claim 19 wherein said containment dam defines a height of at least about 0.5 centimeters and a compression resistance of at least about 50 percent.

27. A disposable absorbent article having a front waist section, a rear waist section, an intermediate section which interconnects said front and rear waist sections, a pair of longitudinally opposed end edges, and a pair of laterally opposed side edges, said article comprising:
   a) a backsheet layer;
   b) a topsheet layer which is connected in superposed relation to said backsheet layer and which defines an opening therein for receiving fecal exudates wherein said topsheet layer includes elastic members adjacent each lateral edge of said opening to maintain said opening in contact with said wearer's buttocks in use;
   c) an absorbent body which is located between said topsheet layer and said backsheet layer; and
   d) a pair of longitudinally extending, compression resistant containment barriers which are located in a laterally spaced apart relation between said absorbent body and said topsheet layer of said absorbent article and which are configured to provide a void space between a wearer's buttocks and said absorbent body of said absorbent article for containing fecal exudates wherein an inner edge of each of said containment barriers defines a plurality of recesses which define a depth in a lateral direction towards an outer edge of said respective containment barrier and away from a longitudinal centerline of said absorbent article.

28. The absorbent article according to claim 27 wherein each of said containment barriers defines a length, a width, a height, a width to height ratio of at least about 0.5, and a compression resistance of at least about 50 percent.

29. The absorbent article according to claim 28 wherein said width of each of said containment barriers is at least about 7 percent of a width of said absorbent article measured along a lateral centerline of said absorbent article.

30. The absorbent article according to claim 28 wherein said height of each of said containment barriers is at least about 0.5 centimeters.

31. The absorbent article according to claim 28 wherein said length of each of said containment barriers is at least about 15 percent of a length of said absorbent article and wherein at least about 50 percent of said length of each of said containment barriers is located rearward of a lateral centerline of said absorbent article.

32. The absorbent article according to claim 27 wherein said containment barriers are laterally spaced apart a distance of no more than about 8 centimeters.

33. The absorbent article according to claim 27 wherein each of said containment barriers defines an inner edge and an outer edge and wherein a height of said containment barrier at said inner edge is less than a height of said containment barrier at said outer edge.

34. The absorbent article according to claim 27 wherein said depth of each of said recesses in said lateral direction is at least about 0.5 centimeters.

35. The absorbent article according to claim 27 wherein said opening in said topsheet layer defines a length of at least about 20 percent of a length of said absorbent article and wherein at least about 50 percent of said length of said opening is located rearward of a lateral centerline of said absorbent article.

36. The absorbent article according to claim 27 wherein said opening in said topsheet layer defines a pair of laterally opposed edges which diverge laterally outward in said rear waist section of said absorbent article.

37. The absorbent article according to claim 27 wherein said opening in said topsheet layer defines a width along a lateral centerline of said absorbent article of at least about 20 percent of a width of said absorbent article along said lateral centerline.

38. The absorbent article according to claim 27 wherein said opening defines an area of at least about 10 square centimeters.

39. The absorbent article according to claim 27 and further comprising at least one compression resistant, containment dam which is located between said absorbent body and said topsheet layer in said rear waist section of said absorbent article and which is configured to inhibit a longitudinal flow of fecal exudates.

40. The absorbent article according to claim 39 wherein said containment dam is located longitudinally inward from an end edge of said rear waist section of said absorbent article a distance of at least about 10 percent of a length of said absorbent article.

41. The absorbent article according to claim 39 wherein said containment dam defines a height of at least about 0.5 centimeters and a compression resistance of at least about 50 percent.

* * * * *